United States Patent [19]
Pennetreau et al.

[11] Patent Number: 5,545,772
[45] Date of Patent: Aug. 13, 1996

[54] PROCESS FOR THE PREPARATION OF 1,1,1-TRIFLUOROETHANE

[75] Inventors: Pascal Pennetreau, Rixensart; Dominique Balthasart, Brussels, both of Belgium

[73] Assignee: Solvay (Société Anonyme), Brussels, Belgium

[21] Appl. No.: 533,308

[22] Filed: Sep. 25, 1995

[30] Foreign Application Priority Data

Sep. 26, 1994 [FR] France ................... 94 11563

[51] Int. Cl.$^6$ .................................................. C07C 17/08
[52] U.S. Cl. .................................................. 570/164
[58] Field of Search .................................. 570/164

[56] References Cited

U.S. PATENT DOCUMENTS

| | | |
|---|---|---|
| 2,669,590 | 2/1954 | Miller et al. . |
| 3,836,479 | 9/1974 | Pansksch et al. . |
| 5,008,474 | 4/1991 | Wairaevens et al. . |
| 5,367,102 | 11/1994 | Janssens et al. . |
| 5,382,721 | 1/1995 | Pennetreau et al. . |

FOREIGN PATENT DOCUMENTS

| | | |
|---|---|---|
| 0391102 | 10/1990 | European Pat. Off. . |
| 574077 | 12/1993 | European Pat. Off. . |
| 2124239 | 9/1972 | France . |
| 2365542 | 4/1978 | France . |
| WO91/18852 | 12/1991 | WIPO . |

OTHER PUBLICATIONS

G. A. Olah et al; Journal of Organic Chemistry, "Organic Fluorine Compounds. XXXIII Electrophilic Additions to Fluoro Olefins in Superacids", 1972, vol. 37, No. 7.

*Primary Examiner*—Alan Siegel
*Attorney, Agent, or Firm*—Spencer & Frank

[57] ABSTRACT

1,1,1-Trifluoroethane (HFC-143a) is produced in the liquid phase by reaction between vinylidene fluoride and hydrogen fluoride, in the absence of catalyst.

7 Claims, No Drawings

PROCESS FOR THE PREPARATION OF 1,1,1-TRIFLUOROETHANE

The invention relates to a process for the preparation of 1,1,1-trifluoroethane (HFC-143a), by reaction between vinylidene fluoride and hydrogen fluoride in the liquid phase.

It is known, in particular from U.S. Pat. No. 2,669,590, to prepare 1,1,1-trifluoroethane by reaction of vinylidene fluoride with hydrogen fluoride in the gas phase, in the presence of a catalyst. The production efficiency of such a process per unit of reactor volume is, however, very poor.

It is moreover known to prepare 1,1,1-trifluoroethane starting with the same reactants, in the liquid phase, at a temperature of −50° C., in the presence of antimony pentafluoride as catalyst (Olah G. A. and Mo Y. K.; Journal of Organic Chemistry, (1972), Vol. 37, No.7). In such a process, the heavy by-products formed in small amounts are contaminated with the heavy metals used as catalysts. In addition, the antimony pentafluoride is gradually converted into antimony trifluoride, which is particularly corrosive towards metallic materials.

The present invention is consequently directed towards providing a process for the preparation of 1,1,1-trifluoroethane, which no longer has the drawbacks of the processes mentioned above and which can be readily carried out industrially.

The invention consequently relates to a process for the preparation of 1,1,1-trifluoroethane by reaction between vinylidene fluoride and hydrogen fluoride in the liquid phase, which process is characterized in that the reaction is performed in the absence of catalyst. The term catalyst refers to any compound which substantially increases the rate of reaction.

Indeed, it has been observed, surprisingly, that vinylidene fluoride and hydrogen fluoride react very rapidly in the liquid phase in the absence of any catalyst, in order to form 1,1,1-trifluoroethane very selectively, whereas in the gas phase, they react very slowly in the absence of catalyst.

In the process according to the invention, vinylidene fluoride and hydrogen fluoride may be used in variable molar ratios. Generally, at least 1 mol of hydrogen fluoride is used per mole of vinylidene fluoride. This ratio is preferably at least about 2. Usually, the amount of hydrogen fluoride does not exceed about 20 mol per mole of vinylidene fluoride. This ratio advantageously does not exceed 10.

The process according to the invention may be performed within a wide range of temperatures. Generally, the process is conducted at a temperature of at least about −50° C. It is preferably at least −30° C. Good results have been obtained at a temperature above or equal to −20° C. The reaction temperature usually does not exceed about 120° C. It advantageously does not exceed 100° C. Good results have been obtained at a temperature not exceeding 90° C.

The pressure at which the process according to the invention is conducted is not critical per se, as long as it allows the reaction to be carried out in the liquid phase, that is to say as long as it is sufficient to maintain the reactants present in the reactor in essentially liquid form. The pressure varies depending on the temperature of the reaction mixture. This pressure may be the autogenous pressure, a higher pressure generated by the introduction of an inert gas, for example such as nitrogen, or a lower pressure obtained by dilution of the reaction mixture with an organic solvent such as, for example, 1,2-dichloroethane, 1,1-dichloro-1-fluoroethane, a chlorofluorobutane of empirical formula $C_4H_5Cl_{5-x}F_x$, where x is a number from 0 to 5, or a mixture of these compounds. The reaction is generally carried out at a pressure at least equal to 2 bar, preferably at least equal to 3 bar. The pressure usually does not exceed 30 bar. It advantageously does not exceed 20 bar.

The process according to the invention may be carried out in a batchwise manner, but it is advantageously carried out in a continuous manner.

The residence time of the reactants in the reactor, that is to say, in batchwise mode, the duration of the reaction and, in continuous mode, the ratio between the volume of the reaction mixture contained in the reactor and the total flow rate of the reactants in the liquid state, is generally at least about 2 minutes. It is preferably at least about 5 minutes. It usually does not exceed about 2 hours. A residence time not exceeding about 1 hour is particularly recommended.

The process according to the invention may be performed in any reactor made of a material which is resistant to the operating temperature and pressure and which is resistant to hydrogen fluoride under the conditions in which the process is carried out. Reactors made of carbon steel, of stainless steel or of alloys such as those known under the trade names MONEL, INCONEL or HASTELLOY are advantageously used. It is also possible to use reactors fitted with a coating made of a hydrogen fluoride-resistant metal or alloy, or coated with a layer of a resin which is inert under the reaction conditions, in particular a fluoro resin.

The process according to the invention has the appreciable advantage of a 1,1,1-trifluoroethane production efficiency which is markedly superior to that achieved by a similar process performed in the gas phase. The process also makes it possible to obtain an excellent selectivity towards 1,1,1-trifluoroethane, the formation of heavy by-products being very limited. It also avoids the formation of sludges resulting from the presence of a catalyst. Furthermore, in the absence of catalysts, the heavy by-products possibly formed are not contaminated with heavy metals and may consequently be destroyed more easily.

The examples which follow illustrate the invention in a non-limiting manner.

EXAMPLE 1 (Comparison)

Gas-phase hydrofluorination

Hydrogen fluoride (HF) and vinylidene fluoride (VF2) in an HF/VF2 molar ratio equal to 3 were introduced, in gas form, into a stainless steel reactor containing no catalytic solid. The reactor was maintained at a temperature of 135° C. and the residence time of the reactants was 13 seconds. Under these conditions the conversion of the VF2 into 1,1,1-trifluoroethane (HFC-143a) was about 7%, equivalent to an average production efficiency for HFC-143a of 12 $g.l^{-1}.h^{-1}$.

EXAMPLE 2

77.8 g of HF and then 20 g of VF2 were introduced into a 0.5 l stainless steel autoclave equipped with a mechanical stirrer, a temperature probe and a dip tube in order to take samples in the liquid phase, this autoclave having been placed under vacuum and cooled to about −60° C. beforehand. After the introduction of the VF2, which lasted 5 minutes, a temperature of −50° C. and a pressure of 3 bar were measured.

15 minutes after the end of the introduction of the VF2, a sample of the liquid phase was taken. The temperature was then −16° C. Analysis of this sample revealed that the conversion of the VF2. was already greater than 99.8% and that all the VF2 was converted into HFC-143a (selectivity= 100%). It may be calculated that the minimum production efficiency for HFC-143a under these conditions is at least 200 $g.l^{-1}.h^{-1}$.

Comparison of the results reported in Examples 1 and 2 indicates that the reactivity between VF2 and HF is much higher in the liquid phase than in the gas phase.

We claim:

1. A process for the preparation of 1,1,1-trifluoroethane by reaction of vinylidene fluoride with hydrogen fluoride in the liquid phase, characterized in that the reaction is performed in the absence of catalyst.

2. The process of claim 1, in which the reaction is performed at a temperature of from −50° to +120° C.

3. The process of claim 2, in which the reaction is performed at a temperature of from −30° to +100° C.

4. The process of claim 1, in which the hydrogen fluoride and the vinylidene fluoride are used in a hydrogen fluoride/vinylidene fluoride molar ratio of from 1 to 20.

5. The process of claim 1, in which the reaction is performed at a pressure of from 2 to 30 bar.

6. The process of claim 1, in which the reaction is performed in a reactor working in a continuous manner.

7. The process of claim 6, in which the process operates with a residence time of the reactants in the reactor of from 1 minute to 2 hours.

* * * * *